United States Patent [19]

Pieles

[11] Patent Number: 5,506,348
[45] Date of Patent: Apr. 9, 1996

[54] MATRIX FOR MATRIX-ASSISTED LASER DESORPTION MASS SPECTROSCOPY

[75] Inventor: Uwe Pieles, Bad Krozingen, Germany

[73] Assignee: Ciba-Geigy Corporation, Tarrytown, N.Y.

[21] Appl. No.: 201,308

[22] Filed: Feb. 24, 1994

[30] Foreign Application Priority Data

Feb. 26, 1993 [CH] Switzerland .............................. 591/93
Jul. 23, 1993 [CH] Switzerland ............................ 2233/93

[51] Int. Cl.$^6$ ............................ C07H 21/04; C12Q 1/68; G01N 24/00; G01N 1/00
[52] U.S. Cl. ........................ 536/23.1; 536/25.4; 568/335; 568/336; 568/337; 435/6; 436/173; 436/174; 436/178
[58] Field of Search ................................ 435/6; 536/23.1, 536/25.4; 568/335, 336, 337; 436/173, 174, 178

[56] References Cited

U.S. PATENT DOCUMENTS 5,045,694  9/1991  Beavis et al. .......................... 250/287
5,118,937  6/1992  Hillenkamp et al. ................... 250/282

FOREIGN PATENT DOCUMENTS 4017804  3/1991  Germany .
9104570  4/1991  WIPO .

OTHER PUBLICATIONS

V. Marquez et al. Carbocyclic Nucleosides, Medicinal Research Rev. vol. 6, No. 1, 1–40 (1986).
Uhlmann, E. et al. Chem. Rev. 90:543–584 (1990).
K. Tang et al. Rapid Comm. in Mass Spectrometry G: 365–368 (1992).
U. Pieles et al. Nucleic Acids Research, 1993, vol. 21, No. 14, pp. 3191–3196.
G. Parr et al. Rapid Comm in Mass Spectrometry vol. 6, pp. 369–372 (1992).
U. Einglisch et al. Angewandte Chemie , Int. Ed. (Eng.) vol. 30, No. 6 1991 pp. 613–629.

*Primary Examiner*—John W. Rollins
*Assistant Examiner*—Francisco C. Prats
*Attorney, Agent, or Firm*—George R. Dohmann

[57] ABSTRACT

The invention relates to a composition comprising (a) at least one ammonium salt of an inorganic or organic acid, (b) a compound of formula I

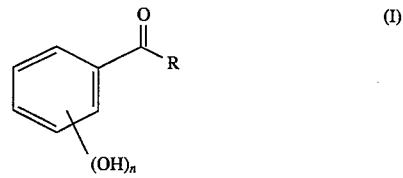

wherein R is an aliphatic hydrocarbon radical of 1 to 12 carbon atoms or an aliphatic hydrocarbon radical of 2 to 12 carbon atoms which is interrupted by —O— atoms, and n is an integer from 1 to 5, and (c) at least one high molecular weight compound selected from the group consisting of the polynucleotides, oligosaccharides, proteins and macrocyclic metal complexes, and to the use thereof for the matrix-assisted laser desorption mass spectroscopy of oligonucleotide sequences.

15 Claims, No Drawings

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
( A ) LENGTH: 8 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

AGCTAGCT                                                                                                                    8

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AATCAGGTAA CCCGCATAGT GAAGTATAGC TTCGACCTA                                                                                   39

( 2 ) INFORMATION FOR SEQ ID NO:3:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

TTACGCCTAA CAGCGATATC AGGACTTCAG CGTACAGCAT TACCAGTATA GCCTTAGAGC                                                             60

( 2 ) INFORMATION FOR SEQ ID NO:4:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AATCAGGTAA CCCGCATAGT GAAGTATAGC TTCG                                                                                        34

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

NNNCAGGTAA CCCGCATAGT GAAGTATAGC TTCG                                                                                        34

( 2 ) INFORMATION FOR SEQ ID NO:6:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

NNNCAGGTAA CCCGCATAGT GAAGTATAGC TTC 33

(2) INFORMATION FOR SEQ ID NO:7:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

NNNCAGGTAA CCCGCATAGT GAAGTATAGC TT 32

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

NNNCAGGTAA CCCGCATAGT GAAGTATAGC T 31

(2) INFORMATION FOR SEQ ID NO:9:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

NNNCAGGTAA CCCGCATAGT GAAGTATAGC 30

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

NNNCAGGTAA CCCGCATAGT GAAGTATAG 29

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

NNNCAGGTAA CCCGCATAGT GAAGTATA 28

(2) INFORMATION FOR SEQ ID NO:12:

( i ) SEQUENCE CHARACTERISTICS:
 ( A ) LENGTH: 27 base pairs
 ( B ) TYPE: nucleic acid
 ( C ) STRANDEDNESS: single
 ( D ) TOPOLOGY: linear ( i i ) MOLECULE TYPE: DNA (genomic)

( x i ) SEQUENCE DESCRIPTION: SEQ ID NO:12:

NNNCAGGTAA CCCGCATAGT GAAGTAT  27

( 2 ) INFORMATION FOR SEQ ID NO:13:

( i ) SEQUENCE CHARACTERISTICS:
  ( A ) LENGTH: 26 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:13:

NNNCAGGTAA CCCGCATAGT GAAGTA  26

( 2 ) INFORMATION FOR SEQ ID NO:14:

( i ) SEQUENCE CHARACTERISTICS:
  ( A ) LENGTH: 25 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:14:

NNNCAGGTAA CCCGCATAGT GAAGT  25

( 2 ) INFORMATION FOR SEQ ID NO:15:

( i ) SEQUENCE CHARACTERISTICS:
  ( A ) LENGTH: 24 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:15:

NNNCAGGTAA CCCGCATAGT GAAG  24

( 2 ) INFORMATION FOR SEQ ID NO:16:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:16:

NNNCAGGTAA CCCGCATAGT GAA  23

( 2 ) INFORMATION FOR SEQ ID NO:17:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:17:

NNNCAGGTAA CCCGCATAGT GA 22

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

NNNCAGGTAA CCCGCATAGT G 21

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

NNNCAGGTAA CCCGCATAGT 20

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

NNNCAGGTAA CCCGCATAG 19

( 2 ) INFORMATION FOR SEQ ID NO:21:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

NNNCAGGTAA CCCGCATA 18

( 2 ) INFORMATION FOR SEQ ID NO:22:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

NNNCAGGTAA CCCGCAT 17

( 2 ) INFORMATION FOR SEQ ID NO:23:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

NNNCAGGTAA CCCGCA 16

( 2 ) INFORMATION FOR SEQ ID NO:24:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

NNNCAGGTAA CCCGC 15

( 2 ) INFORMATION FOR SEQ ID NO:25:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:25:

NNNCAGGTAA CCCG 14

( 2 ) INFORMATION FOR SEQ ID NO:26:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

NNNCAGGTAA CCC 13

( 2 ) INFORMATION FOR SEQ ID NO:27:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

NNNCAGGTAA CC 12

( 2 ) INFORMATION FOR SEQ ID NO:28:

(i) SEQUENCE CHARACTERISTICS:
   (A) LENGTH: 11 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:28:

NNNCAGGTAA C  11

(2) INFORMATION FOR SEQ ID NO:29:

(i) SEQUENCE CHARACTERISTICS:
   (A) LENGTH: 10 base pairs
   (B) TYPE: nucleic acid
   (C) STRANDEDNESS: single
   (D) TOPOLOGY: linear (ii) MOLECULE TYPE: DNA (genomic)

(xi) SEQUENCE DESCRIPTION: SEQ ID NO:29:

NNNCAGGTAA  10

MATRIX FOR MATRIX-ASSISTED LASER DESORPTION MASS SPECTROSCOPY

The present invention relates to a composition that contains a phenone which is substituted in the phenyl nucleus, an ammonium salt and a high molecular weight compound, and to the use of said composition for the matrix-assisted laser desorption mass spectroscopy of oligonucleotide sequences.

Matrix-assisted laser desorption mass spectroscopy makes it possible to determine molecular weights of peptides and proteins of a few hundred to more than 100 000 Dalton. For this utility, the matrix in which the protein is embedded is an important factor. DE-A-40 17 804 and WO 91/04570 disclose compounds which are used as matrices in the laser desorption mass spectroscopy of biomolecules. Comparable experiments for determining the molecular weight of oligonucleotides have so far been only of limited success and are described by, inter alia, G. R. Parr et al., Rapid Communications in Mass Spectrometry, Vol. 6, pages 369–372 (1992) and by K. Tang et al., Rapid Communications in Mass Spectrometry, Vol. 6, pages 365–368 (1992). In the methods described in these references, provided a laser desorption can be achieved at all, there are observed in the case of small oligonucleotides a number of mass peaks which can be explained by the formation of adducts containing $Na^+$ and $K^+$ and, in the case of larger oligonucleotides, broad peaks which permit only a very inaccurate mass determination. There is therefore keen interest in providing new matrices for the laser desorption of oligonucleotide ions.

In one of its aspects, the invention relates to a composition comprising (a) at least one ammonium salt of an inorganic or organic acid, (b) a compound of formula I

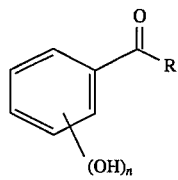

wherein R is an aliphatic hydrocarbon radical of 1 to 12 carbon atoms or an aliphatic hydrocarbon radical of 2 to 12 carbon atoms which is interrupted by —O— atoms, and n is an integer from 1 to 5, and (c) at least one high molecular weight compound selected from the group consisting of the polynucleotides, oligosaccharides, proteins and macrocyclic metal complexes.

The compound of formula I and the ammonium salt are preferably in a molar ratio of 1:5 to 1:20 and, most preferably, from 1:8 to 1:12. The high molecular weight compound and the compound of formula I are preferably used in a molar ratio of $1:5\times10^3$ to $1:5\times10^5$, most preferably of $1:10^4$ to $1:10^5$.

The high molecular weight compounds may typically be poly- and oligonucleotides of the RNA and DNA type, oligosaccharides consisting preferably of 2–10 sugar units linked by glycosidic bonds, peptides and proteins consisting of naturally occuring and/or synthetically prepared amino acids, or metal complexes with macrocyclic ligands containing hetero atoms, typically crown ethers and $Na^+$-ionophor nonactine. It is particularly preferred to use poly- and oligonucleotides that consist of natural or synthetic nucleoside residues or mixtures of such nucleoside residues. The oligonucleotides used may consist of 2 to 200, preferably of 2 to 100 and, more particularly, of 2 to 60, most preferably of 2 to 40, nucleoside residues. It is immaterial whether the nucleoside residues are naturally occurring or synthetically modified nucleoside residues. Natural nucleoside residues may be adenosine, guanosine, cytidine, uridine, 2'-desoxyadenosine, 2'-desoxythymidine, 2'-desoxyguanosine and 2'-desoxycytidine. Among the modified nucleoside residues, those nucleoside residues are to be highlighted which are derived from adenine, N-methyladenine, 2-aminoadenine, 6-hydroxypurine, 2-amino-6-chloropurine, 2-amino-6-methylthiopurine, guanine, 7-deazaguanine, N-isobutyrylguanine, uracil, thymine, cytosine, 5-fluorouracil, 5-chlorouracil, 5-bromouracil, dihydrouracil and 5-methylcytosin, as well as their phosphonates, phosphorothioates, phosphoroamidates, dephospho derivatives and carbocyclic derivatives. A whole host of synthetic nucleoside residues are known and described, inter alia, in E. Uhlmann et al, Chemical Reviews, Vol. 90, pages 543–584 (1990); V. Marquez et al, Medicinal Research Reviews, Vol. 6, pages 1–40 (1986); and U. Englisch et al. Angewandte Chemie, No. 6, pages 629–739 (1991).

In the compounds embraced by formula I, R may be linear or branched $C_1$–$C_{12}$alkyl, $C_1$–$C_{12}$hydroxyalkyl, $C_5$–$C_7$cycloalkyl, $C_5$–$C_7$hydroxycycloalkyl, linear or branched $C_2$–$C_{12}$alkyl or $C_2$–$C_{12}$hydroxyalkyl interrupted by —O— atoms, $C_5$–$C_7$cycloalkyl or $C_5$–$C_7$hydroxycycloalkyl interrupted by —O— atoms, or hydrogen. Preferred compounds of formula I are those in which R is linear or branched alkyl or cycloalkyl. Linear or branched $C_1$–$C_4$alkyl is especially preferred. Typical examples of compounds of formula I are 2,4,6-trihydroxyacetophenone, 2,4,5-trihydroxybutyrophenone, 2,4-, 2,5- and 2,6-dihydroxyacetophenone.

Surprisingly, it has been found that the presence of an ammonium salt of an inorganic or organic acid is the key component of the novel composition. This ammonium salt may be the ammonium salt of a hydrohalic acid, of perchloric acid, chalcogenic acid, nitric acid, nitrous acid, carbonic acid and boric acid, of a hydroxypolycarboxylic acid or of an acid HOOC—$R_1$—COOH, wherein $R_1$ is $C_1$–$C_8$alkylene, $C_5$–$C_6$cycloalkylene, phenylene or naphthylene containing 1 to 3 hydroxyl groups. In conjunction with oligonucleotides and a compound of formula I, they not only make possible the laser desorption of oligonucleotide ions regardless of their base sequence, but at the same time they prevent the formation of adducts containing e.g. $Na^+$ and $K^+$. When using the novel composition for matrix-assisted laser desorption mass spectroscopy, this feature results in sharp molecular peaks of the oligonucleotide ions whose corresponding molecular mass can be determined exactly. It is preferred to use the salts of sulfuric acid, nitric acid, tartronic acid, malic acid. tartaric acid, citric acid as well as of the acids HOOC—$R_1$—COOH, wherein $R_1$ is $C_1$–$C_8$alkylene, $C_5$–$C_6$cycloalkylene, phenylene or naphthylene containing 1 to 3 hydroxyl groups. Among these salts, the ammonium salts of sulfuric acid, tartaric acid and citric acid are especially preferred.

A typical composition of this invention is weakly acidic with a pH of c. 6 and contains at least one ammonium salt of, for example, sulfuric acid, tartaric acid or citric acid, as compound of formula I, typically 2,4,6-trihydroxyacetophenone, 2,4,5-trihydroxybutyrophenone, 2,4-, 2,5- or 2,6-dihydroxyacetophenone as well as at least one oligonucleotide consisting of natural or synthetic nucleoside residues or mixtures of said nucleoside residues.

The use of the novel composition for the matrix-assisted laser desorption mass spectroscopy of oligonucleotides is of particular importance.

In another of its aspects, the invention relates to a composition for use as matrix for the laser desorption of analyte molecular ions, which composition comprises at least one ammonium salt of an inorganic or organic acid and a compound of formula I

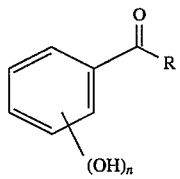

wherein R and n have the meanings previously assigned to them. The ratio of ammonium salt to compound of formula I is preferably 1:5 to 1:20, but most preferably 1:8 to 1:12.

The invention further relates to a method of determining the molecular weights of oligonucleotides containing 2 to 200, preferably 2 to 100 and, more particularly 2 to 60, most preferably 2 to 40, nucleosides residues by means of matrix-assisted laser desorption mass spectroscopy, wherein the the above described novel composition is used as matrix for the laser desorption. The process comprises first mixing a compound of formula I, ammonium salt and oligonucleotide in a solvent, coating the probe support with a portion of the solution and, finally, gently removing the solvent by evaporation. The crystallised probe can then be used for the matrix-assisted laser desorption mass spectroscopy, using preferably nitrogen lasers that emit a wavelength of 337 nm. The amount of nucleotide is preferably so chosen that the molar ratio of oligonucleotide to compound of formula I is $1:5\times10^3$ to $1:5\times10^5$, most preferably $1:10^4$ bis $1:10^5$. The matrices of this invention permit good accord of the experimental molecular weight determination with the calculated values. Surprisingly, the compounds of formula I, wherein n is 2, are especially suitable for determining the molecular weight of oligonucleotides containing more than 25 nucleotide units and of phosphorothioates.

With the aid of this process it is now possible not only to determine the molecular weight of an oligonucleotide, but also the exact sequence of its nucleoside residues. To this end, the oligonucleotide is degraded nucleotide by nucleotide selectively from the 5'-end and selectively from the 3'-end in separate reactions. This is done by using enzymes, so-called 5'-exonucleases and 3'-exonucleases, which are used either in water or in the requisite buffer. It is particularly preferred to use calf spleen phosphodiesterase and snake venom phosphodiesterase. This degradation, depending on the incubation time, results in the formation of different mixtures of oligonucleotides of varying length. If the enzymes are used in the requisite buffer, then these mixtures of oligonucleotides are deionised by methods generally known in the art, for example by microdialysis. Afterwards the mixtures are characterised by matrix-assisted laser desorption mass spectroscopy. The eliminated nucleotide can be inferred and thus the complete nucleotide sequence determined from the differences in mass between the individual molecular peaks. Compared with the alternative sequencing method of molecular biology, the novel process is distinguished on the one hand by its speed and, on the other, no toxic or radioactive substances are required.

Furthermore, this process opens up new and still unknown possibilities of characterising oligonucleotides. Thus, for example, the simple molecular weight determination of an oligonucleotide of known sequence makes possible the rapid and unequivocal detection of the presence of a modified or synthetic nucleoside residue. After degradation of the oligonucleotides with 5'- or 3'-exonucleases it is also often possible to determine the position of the modified base within the oligonucleotide, as exonucleases are usually unable to degrade non-natural modified nucleoside residues under specific conditions easily ascertainable by those skilled in the art. In this case the degradation of the oligonucleotide at the modified nucleoside residue comes to a standstill, thereby resulting in a single signal of the corresponding oligonucleotide fragment in the mass spectrum.

The following Examples illustrate the invention in more detail.

A) Preparative Examples

Preparation of the Composition

EXAMPLE A1

5 µl of a 1M solution of 2,4,6-trihydroxyacetophenone, 5 µl of a 0.1M solution of ammonium sulfate and 5 µl of ethanol are mixed with 1 µl of a 50 µM solution of the oligonucleotide A, SEQ ID NO:1, having the base sequence 5'-AGCTAGCT-3'. 1 µl of this solution is applied to a probe support and the solvent is gently removed under vacuum. The composition so prepared can then be used for matrix-assisted laser desorption mass spectroscopy.

EXAMPLE A2

5 µl of a 1M solution of 2,4,6-trihydroxyacetophenone, 5 µl of a 0.1M solution of ammonium dihydrogen citrate and 5 µl of ethanol are mixed with 1 µl of a 50 µM solution of oligonucleotide B, SEQ ID NO:2, having the base sequence 5'-d(AAT CAG GTA ACC CGC ATA GTG AAG TAT AGC TTC GAC CTA)-3'. 1 µl of this solution is applied to a probe support and the solvent is gently removed under vacuum. The composition so prepared can then be used for matrix-assisted laser desorption mass spectroscopy.

EXAMPLE A3

5 µl of a 1M solution of 2,6-dihydroxyacetophenone, 5 µl of a 0.1M solution of ammonium dihydrogen citrate and 5 µl of ethanol are mixed with 1 µl of a 50 µM solution of oligonucleotide B, SEQ ID NO:2, having the base sequence 5'-d(AAT CAG GTA ACC CGC ATA GTG AAG TAT AGC TTC GAC CTA)-3'. 1 µl of this solution is applied to a probe support and the solvent is gentyl removed under vacuum. The composition so prepared can then be used for matrix-assisted laser desorption mass spectroscopy.

EXAMPLE A4

5 µl of a 1M solution of 2,6-dihydroxyacetophenone, 5 µl of a 0.1M solution of ammonium dihydrogen citrate and 5 µl of ethanol are mixed with 1 µl of a 50 µM solution of oligonucleotide C, SEQ ID NO:3, having the base sequence 5'-d(TTA CGC CTA ACA GCG ATA TCA GGA CTT CAG CGT ACA GCA TTA CCA GTA TAG CCT TAG AGC)-3'. 1 µl of this solution is applied to a probe support and the solvent is gently removed under vacuum. The composition so prepared can then be used for matrix-assisted laser desorption mass spectroscopy.

Use Examples

Molecular Weight Determination

EXAMPLE B1

Phenylalanyl-tRNA from brewer's yeast is prepared as described in Example A1 for molecular weight determination and then analysed by matrix-assisted laser desorption massspectroscopy with a laser of 337 nm wavelength.

The mass spectrum shows a main peak at 24 877.3 g/mol and a secondary peak at 12 578.0 g/mol. The main peak corresponds to the molecular ion of phenylalanyl-tRNA carrying a single charge, and the secondary peak corresponds to the molecular ion carrying a double charge.

EXAMPLE B2

The oligonucleotide B, SEQ ID NO:2, having the base sequence 5'-d(AAT CAG GTA ACC CGC ATA GTG AAG TAT AGC TTC GAC CTA)-3' is prepared as described in Example A2 for molecular weight determination and then analysed by matrix-assisted laser desorption massspectroscopy with a laser of 337 nm wavelength.

The mass spectrum shows a peak at 12 122.3 g/mol compared with a calculated mass of 12 272.1 (molecule minus one proton).

EXAMPLE B3

The oligonucleotide B, SEQ ID NO:2, having the base sequence 5'-d(AAT CAG GTA ACC CGC ATA GTG AAG TAT AGC TTC GAC CTA)-3' is prepared as described in Example A3 for molecular weight determination and then analysed by matrix-assisted laser desorption massspectroscopy with a laser of 337 nm wavelength.

The mass spectrum shows a peak at 12 278.3 g/mol compared with a calculated mass of 12 274.1 (molecule plus one proton).

EXAMPLE B4

The oligonucleotide C, SEQ ID NO:3, having the base sequence 5'-d(TTA CGC CTA ACA GCG ATA TCA GGA CTT CAG CGT ACA GCA TTA CCA GTA TAG CCT TAG AGC)-3' is prepared as described in Example A4 for molecular weight determination and then analysed by matrix-assisted laser desorption massspectroscopy with a laser of 337 nm wavelength.

The mass spectrum shows a peak at 18 453.8 g/mol compared with a calculated mass of 18 453.1 (molecule plus one proton).

Sequencing

EXAMPLE C1

The sequencing of the oligonucleotide A, SEQ ID NO:1, (5'-AGCTAGCT-3') is carried out by exonucleolytic degradation from both the 5'-end and from the 3'-end in separate reactions.

For degradation from the 5'-end, a mixture of 20 µl of a 50 µM solution of the oligonucleotide A and 1 µl of a solution of calf spleen phosphodiesterase enzyme (2×10⁻³U/µl) is incubated at 37° C. 1 µl samples prepared as described in Example A1 are taken every 15 minutes and then characterised by matrix-assisted laser desorption mass spectroscopy.

For degradation from the 3'-end, 20 µl of a mixture of a 50 µM solution of oligonucleotide A and 1 µl of a solution of snake venom phosphodiesterase enzyme (3×10⁻³U/µl) is incubated at 37° C. 1 µl samples prepared as described in Example A1 are taken every 15 minutes and then characterised by matrix-assisted laser desorption mass spectroscopy.

The results obtained are as follows:

| Molecular weight | Fragment |
|---|---|
| Oligonucleotide fragments of the 5'-end degradation - Molecular weights in g/mol | |
| 2405.9 | 5'-AGCTANNN-3' |
| 2092.6 | 5'-GCTANNN-3' |
| 1763.4 | 5'-CTANNN-3' |
| 1474.3 | 5'-TANNN-3' |
| 1170.2 | 5'-ANNN-3' |
| 857.3 | 5'-NNN-3' |
| Oligonucleotide fragments of the 3'-end degradation- Molecular weights in g/mol | |
| 2405.2 | 5'-NNNTAGCT-3' |
| 2100.8 | 5'-NNNTAGC-3' |
| 1811.7 | 5'-NNNTAG-3' |
| 1482.7 | 5'-NNNTA-3' |
| 1169.6 | 5'-NNNT-3' |
| 866.0 | 5'-NNN-3' |
| expected sequence: | 5'-AGCTAGCT-3' |
| determined sequence: | 5'-AGCTAGCT-3' |

EXAMPLE C2

The sequencing of the oligonucleotide D, SEQ ID NO:4, (5'-d(AAT CAG GTA ACC CGC ATA GTG AAG TAT AGC TTC G)-3' is carried out by exonucleolytic degradation from both the 5'-end and from the 3'-end in separate reactions.

For degradation from the 5'-end, a mixture of 20 µl of a 50 µM solution of the oligonucleotide D and 1 µl of a solution of calf spleen phosphodiesterase enzyme (2×10⁻³U/µl) is incubated at 37° C. 1 µl samples prepared as described in Example A3 are after 3 and after 13 minutes and then characterised by matrix-assisted laser desorption mass spectroscopy.

For degradation from the 3'-end, 20 µl of a mixture of a 50 µM solution of oligonucleotide D and 1 µl of a solution of snake venom phosphodiesterase enzyme (3×10⁻³U/µl) is incubated at 37° C. 1 µl samples prepared as described in Example A3 are taken after 3, 30 and 60 minutes, and then characterised by matrix-assisted laser desorption mass spectroscopy.

The results obtained are as follows:

| Molecular weight | Fragment |
|---|---|
| Oligonucleotide fragments of the 5'-end degradation - Molecular weights in g/mol | |
| 10461.2 | 5'-ANNNNNN . . . -3' |
| 10150.2 | 5'-AANNNN . . . -3' |

| Molecular weight | Fragment |
|---|---|
| 9548.0 | 5'-AATNN . . . -3' |

Oligonucleotide fragments of the 3'-end degradation - Molecular weights in g/mol

| | | |
|---|---|---|
| SEQ ID NO:5 | 5'-NNNCAGGTAACCCGCATAGTGAAGTATAGCTTCG-3' | |
| 10467.0 | | |
| SEQ ID NO:6 | 5'-NNNCAGGTAACCCGCATAGTGAAGTATAGCTTC-3' | |
| 10124.6 | | |
| SEQ ID NO:7 | 5'-NNNCAGGTAACCCGCATAGTGAAGTATAGCTT-3' | |
| 9832.5 | | |
| SEQ ID NO:8 | 5'-NNNCAGGTAACCCGCATAGTGAAGTATAGCT-3' | |
| 9530.9 | | |
| SEQ ID NO:9 | 5'-NNNCAGGTAACCCGCATAGTGAAGTATAGC-3' | |
| 9228.2 | | |
| SEQ ID NO:10 | 5'-NNNCAGGTAACCCGCATAGTGAAGTATAG-3' | |
| 8938.0 | | |
| SEQ ID NO:11 | 5'-NNNCAGGTAACCCGCATAGTGAAGTATA-3' | |
| 8614.1 | | |
| SEQ ID NO:12 | 5'-NNNCAGGTAACCCGCATAGTGAAGTAT-3' | |
| 8299.6 | | |
| SEQ ID NO:13 | 5'-NNNCAGGTAACCCGCATAGTGAAGTA-3' | |
| 7995.8 | | |
| SEQ ID NO:14 | 5'-NNNCAGGTAACCCGCATAGTGAAGT-3' | |
| 7684.9 | | |
| SEQ ID NO:15 | 5'-NNNCAGGTAACCCGCATAGTGAAG-3' | |
| 7379.0 | | |
| SEQ ID NO:16 | 5'-NNNCAGGTAACCCGCATAGTGAA-3' | |
| 7098.0 | | |
| SEQ ID NO:17 | 5'-NNNCAGGTAACCCGCATAGTGA-3' | |
| 6783.9 | | |
| SEQ ID NO:18 | 5'-NNNCAGGTAACCCGCATAGTG-3' | |
| 6467.0 | | |
| SEQ ID NO:19 | 5'-NNNCAGGTAACCCGCATAGT-3' | |
| 6135.5 | | |
| SEQ ID NO:20 | 5'-NNNCAGGTAACCCGCATAG-3' | |
| 5829.2 | | |
| SEQ ID NO:21 | 5'-NNNCAGGTAACCCGCATA-3' | |
| 5499.4 | | |
| SEQ ID NO:22 | 5'-NNNCAGGTAACCCGCAT-3' | |
| 5185.7 | | |
| SEQ ID NO:23 | 5'-NNNCAGGTAACCCGCA-3' | |
| 4879.5 | | |
| SEQ ID NO:24 | 5'-NNNCAGGTAACCCGC-3' | |
| 4564.9 | | |
| SEQ ID NO:25 | 5'-NNNCAGGTAACCCG-3' | |
| 4272.9 | | |
| SEQ ID NO:26 | 5'-NNNCAGGTAACCC-3' | |
| 3941.9 | | |
| SEQ ID NO:27 | 5'-NNNCAGGTAACC-3' | |
| 3638.1 | | |
| SEQ ID NO:28 | 5'-NNNCAGGTAAC-3' | |
| 3349.1 | | |
| SEQ ID NO:29 | 5'-NNNCAGGTAA-3' | |
| 3059.8 | | |
| 2747.0 | 5'-NNNCAGGTA-3' | |
| 2433.8 | 5'-NNNCAGGT-3' | |
| 2129.4 | 5'-NNNCAGG-3' | |
| 1800.6 | 5'-NNNCAG-3' | |
| 1471.3 | 5'-NNNCA-3' | |
| 1157.7 | 5'-NNNC-3' | |
| 868.2 | 5'-NNN-3' | |

What is claimed is:

1. A composition comprising
   (a) at least one ammonium salt of an inorganic or organic acid selected from the group consisting of a hydrohalic acid, perchloric acid, chalcogenic acid, nitric acid, nitrous acid, carbonic acid, boric acid, hydroxypolycarboxylic acid and an acid of the formula HOOC—$R_1$—COOH, wherein $R_1$ is $C_1$–$C_8$alkylene, $C_5$–$C_6$cycloalkylene, phenylene or naphthylene containing 1 to 3 hydroxyl groups,
   (b) a compound of formula I

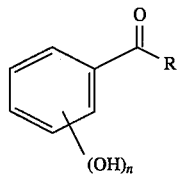

wherein R is an aliphatic hydrocarbon radical of 1 to 12 carbon atoms or an aliphatic hydrocarbon radical of 2 to 12 carbon atoms which is interrupted by —O— atoms, and n is an integer from 1 to 5, and
   (c) at least one high molecular weight compound selected from the group consisting of the polynucleotides, oligosaccharides, proteins and macrocyclic metal complexes.

2. A composition according to claim 1, wherein the ammonium salt and the compound of formula I are in a molar ratio of 1:5 to 1:20.

3. A composition according to claim 1, wherein the high molecular weight compound and the compound of formula I are in a molar ratio of $1:5\times10^3$ to $1:5\times10^5$.

4. A composition according to claim 1, wherein the high molecular weight compound is an oligonucleotide consisting of 2 to 100 nucleoside residues.

5. A composition according to claim 1, wherein R in formula I is linear or branched alkyl or cycloalkyl.

6. A composition according to claim 5, wherein R in formula I is linear or branched $C_1$–$C_4$alkyl.

7. A composition according to claim 1, which comprises 2,4,6-trihydroxyacetophenone, 2,4,5-trihydroxybutyrophenone, 2,4-, 2,5- or 2,6-dihydroxyacetophenone as compound of formula I.

8. A composition according to claim 1, which comprises at least one ammonium salt of the series sulfuric acid, nitric acid, tartronic acid, malic acid, tartaric acid, citric acid and of the acids HOOC—$R_1$—COOH, wherein $R_1$ is $C_1$–$C_8$alkylene, $C_5$–$C_6$cycloalkylene, phenylene or naphthylene containing 1 to 3 hydroxyl groups.

9. A composition according to claim 1, wherein the high molecular weight compound is an oligonucleotide that contains the natural nucleoside residues adenosine, guanosine, cytidine, uridine, 2'-desoxyadenosine, 2-'desoxythymidine, 2'-desoxyguanosine and 2'-desoxycytidine.

10. A composition according to claim 1, wherein the high molecular weight compound is an oligonucleotide that contains, in addition to the natural nucleoside residues, nucleoside residues which are derived from adenine, N-methyladenine, 2-aminoadenine, 6-hydroxypurine, 2-amino-6-chloropurine, 2-amino-6-methylthiopurine, guanine, 7-deazaguanine, N-isobutyrylguanine, uracil, thymine, cytosine, 5-fluorouracil, 5-chlorouracil, 5-bromouracil, dihydrouracil and 5-methylcytosine, as well as their phosphonates, phosphorothioates, phosphoroamidates, dephospho derivatives and carbocyclic derivatives.

11. A composition according to claim 1, which comprises
   (a) at least one ammonium salt of the series consisting of sulfuric acid, tartaric acid and citric acid,
   (b) 2,4,6-trihydroxyacetophenone, 2,4,5-trihydroxybutyrophenone, 2,4-, 2,5- or 2,6-dihydroxyacetophenone as compound of formula I,
   (c) at least one oligonucleotide consisting of natural or synthetic nucleoside residues or of a mixture of said nucleoside residues.

12. A composition for use as matrix for the laser desorption of analyte molecular ions, which composition comprises
   (a) at least one ammonium salt of an inorganic or organic acid selected from the group consisting of a hydrohalic acid, perchloric acid, chalcogenic acid, nitric acid, nitrous acid, carbonic acid, boric acid, hydroxypolycarboxylic acid and an acid of the formula HOOC—$R_1$—COOH, wherein $R_1$ is $C_1$–$C_8$alkylene, $C_5$–$C_6$cycloalkylene, phenylene or naphthylene containing 1 to 3 hydroxyl groups, and (b) a compound of formula I

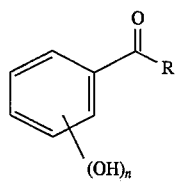
(I)

wherein R is an aliphatic hydrocarbon radical of 1 to 12 carbon atoms or an aliphatic hydrocarbon radical of 2 to 12 carbon atoms which is interrupted by —O— atoms, and n is an integer from 1 to 5.

13. A composition according to claim 12, wherein the ratio of ammonium salt to compound of formula I is 1:5 to 1:20.

14. A composition of claim 1 wherein the high molecular weight compound is an oligionucleotide consisting of 2 to 200 nucleotide residues.

15. A composition of claim 1 wherein the high molecular weight compound is an oligionucleotide consisting of 2 to 40 nucleotide residues.

* * * * *